United States Patent [19]

Wong

[11] Patent Number: 5,384,640
[45] Date of Patent: * Jan. 24, 1995

[54] GAS SAMPLE CHAMBER FOR USE WITH A SOURCE OF COHERENT RADIATION

[75] Inventor: Jacob Y. Wong, Santa Barbara, Calif.

[73] Assignee: Gaztech International Corporation, Goleta, Calif.

[*] Notice: The portion of the term of this patent subsequent to Nov. 17, 2009 has been disclaimed.

[21] Appl. No.: 5,759

[22] Filed: Jan. 19, 1993

[51] Int. Cl.⁶ .................. G01N 21/31; G01N 21/35
[52] U.S. Cl. .................. 356/437; 73/31.02; 250/343
[58] Field of Search .................. 356/437; 73/31.02; 250/343

[56] References Cited

U.S. PATENT DOCUMENTS

| | | | |
|---|---|---|---|
| 4,236,827 | 12/1980 | Horiba et al. | 356/437 |
| 5,015,094 | 5/1991 | Nagai et al. | 356/437 |
| 5,163,332 | 11/1992 | Wong | 356/437 |

*Primary Examiner*—Davis L. Willis
*Assistant Examiner*—LaCharles P. Keesee, II
*Attorney, Agent, or Firm*—Daniel C. McKown

[57] ABSTRACT

A gas sample chamber that is particularly advantageous for use with a semiconductor laser has the form of an elongated hollow tube with a specularly reflective inside surface, a semiconductor laser located at one end of the tube and a detector located at the opposite end of the tube. In one embodiment, apertures in the wall of the tube permit a gas to enter and leave the sample chamber by free diffusion. In another embodiment the gas flows into the hollow tube from a pressurized source through a port or is drawn through the tube by a suction pump. In other embodiments, the tube is partitioned into two successive sections by means of a window located within the tube. The window is transparent to radiation of two different wavelengths that coincide with the absorption bands of two different gases. The semiconductor laser is tuned to these wavelengths successively so that two gas components can be detected and measured simultaneously.

15 Claims, 2 Drawing Sheets

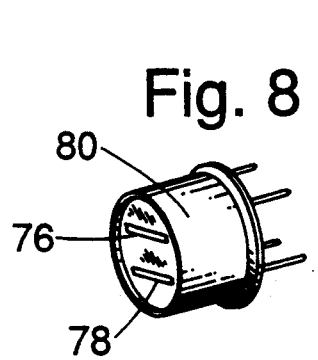
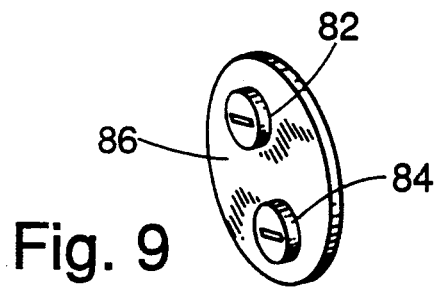
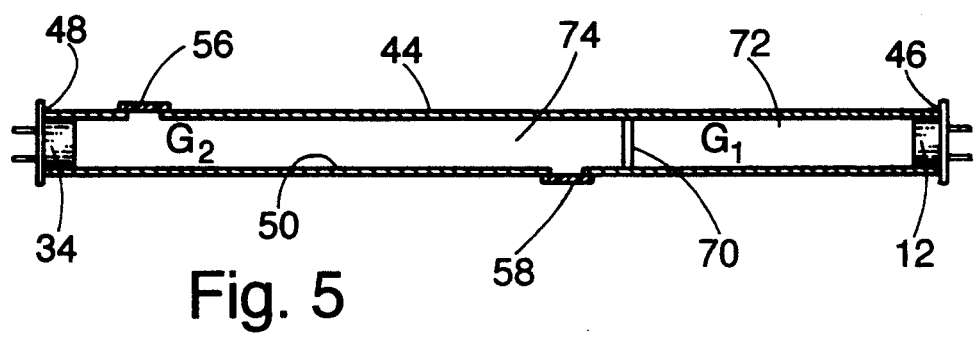
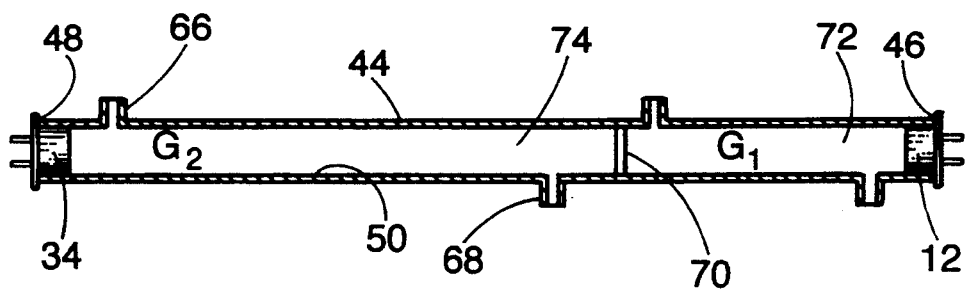
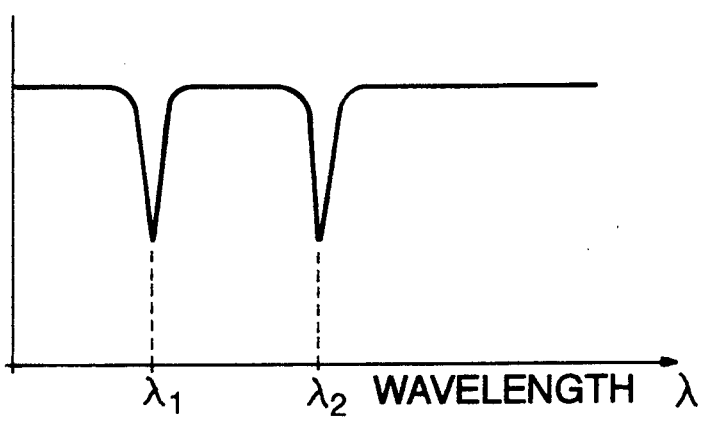

GAS SAMPLE CHAMBER FOR USE WITH A SOURCE OF COHERENT RADIATION

BACKGROUND OF THE INVENTION

1. Field of the Invention

The present invention is in the field of gas analysis and specifically relates to a sample chamber for use with a source of coherent radiation, such as a semiconductor laser, and capable of measuring the concentrations of several gases simultaneously.

2. The Prior Art

Numerous gas sample chambers are known in the art. Normally the design of a gas sample chamber is based on the task which the gas analyzer is expected to perform. The designer has a wide range of components at his disposal, and his design generally consists of a carefully selected combination of components. Each of the following references shows one or more components that are used in the present invention. However, none of the references shows the unique combination that is used in the present invention.

In U.S. Pat. No. 5,060,508 issued Oct. 29, 1991, Wong describes a gas sample chamber consisting of a hollow serpentine passage that extends within a block of a plastic material. An ellipsoidal reflector focuses radiation from a source into the passage, and a detector is located at the other end of the passage.

In U.S. Pat. No. 5,053,754 issued Oct. 1, 1991, Wong describes a fire detector in which a source of radiation, which may be a laser diode, injects radiation having a wavelength corresponding to an absorption band of the gas ($CO_2$) into a hollow passage that guides the radiation along an indirect path to a detector. A semipermeable membrane is used to keep unwanted particles out of the passage.

In Japanese Laid-Open Patent Application No. 59-173734, filed on Mar. 23, 1983 and laid open on Oct. 1, 1984, Miyazaki shows a gas analyzer that has a single source of infrared radiation, a single detector and hollow tubes through which the radiation passes from the source to the detector.

In U.S. Pat. No. 4,709,150, Burough et al. show a gas analyzer in which a source of infrared radiation, which they state could be a semiconductor laser, is located at one end of a porous tube and in which a detector is located at the other end of the porous tube. Burough et al. do not disclose the use of specular reflections from the inside surface of their porous tube. The gas to be detected diffuses through the walls of the porous tube.

In U.S. Pat. No. 5,163,332 issued Nov. 17, 1992, Wong describes a diffusion-type gas sample chamber that employs an elongated hollow tube having a specularly-reflective inner surface and a plurality of filtering apertures each covered by a semipermeable membrane to keep out unwanted particles while permitting free diffusion of gas into and out of the sample chamber.

SUMMARY OF THE INVENTION

A first objective of the present invention is to provide a gas sample chamber that is uniquely suitable for use with a source of coherent radiation and that provides a highly efficient coupling between the source and a detector that receives the radiation after it has passed through the gas sample.

In accordance with the present invention, this objective is accomplished by providing a gas sample chamber in the form of a hollow tube having an inside surface that is specularly reflective. The source of coherent radiation is located at one end of the hollow tube, and a detector of the radiation is located at the opposite end of the tube. The detector is large enough to occupy substantially the entire cross section of the hollow tube, and this permits the detector to receive substantially all of the transmitted radiation. The sample chamber may be operated as a diffusion type sample chamber by providing a number of apertures along its length through which the gas enters and leaves the tube by diffusion. Alternatively, the gas may be forced through the sample chamber by a pressure difference between an entry port and an exist port.

A second objective of the present invention is to provide a gas sample chamber for use with a source of coherent radiation and which is capable of simultaneously measuring two separate gas samples.

In accordance with this aspect of the present invention, the elongated hollow tube described above is partitioned into two non-communicating chambers by the use of a window that is substantially transparent to radiation of wavelengths corresponding to absorption bands of the two gases to be measured. A first gas may be sealed within the first section or may be permitted to enter and leave the first section by diffusion, or may be pumped through the first section. Likewise, the second gas to be measured may be sealed within the second section, or may be permitted to diffuse into and out of the second section through apertures, or may be pumped through the second section. In the preferred embodiment, the source of coherent radiation is tunable between the first absorption wavelength and the second absorption wavelength, and only a single detector is used, which occupies substantially the entire cross section of the hollow tube.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 5 is a diagrammatic cross section view of a gas sample chamber in accordance with a third preferred embodiment of the present invention;

FIG. 6 is a diagrammatic cross section view of a gas sample chamber in accordance with a fourth preferred embodiment of the present invention;

FIG. 7 is a graph showing laser emission spectra and gas absorption bands versus wavelength;

FIG. 8 is a diagram showing a first alternative source; and,

FIG. 9 is a diagram showing a second alternative source.

DETAILED DESCRIPTION OF THE PREFERRED EMBODIMENT

Figure 1:
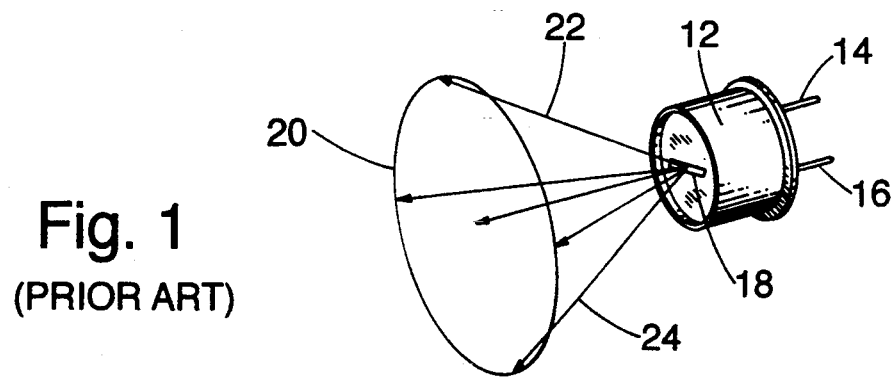
FIG. 1 is a diagrammatic perspective view showing the radiation emission pattern of a semiconductor laser of a type known in the prior art and used in the present invention.

FIG. 1 shows a semiconductor laser 12 of a type known in the art. When an electric current is applied through the pins 14 and 16, radiation is generated at a PN junction. The radiation is emitted in a diverging beam having a cross section 20 of substantially elongated shape. The maximum divergence of the beam is indicated by the rays 22 and 24.

Figure 2:
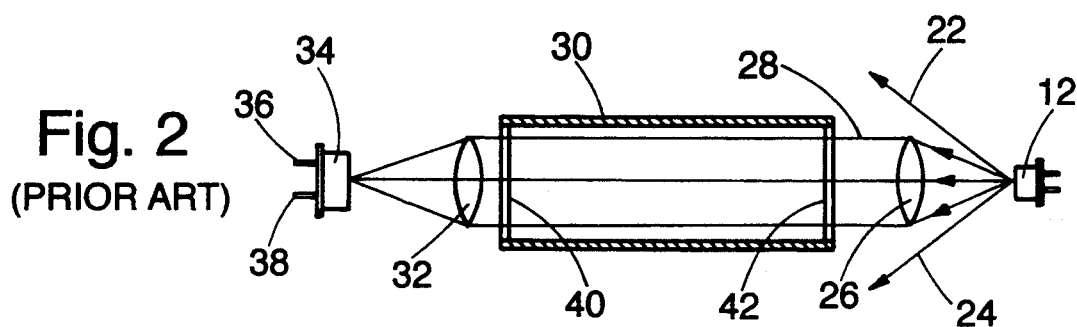
FIG. 2 is a diagram showing a prior art gas sample chamber that uses a collimated beam of radiation.

FIG. 2 shows a typical gas sample chamber of a type used in the prior art. In such a chamber, a collimating lens 26 is provided for the purpose of collecting the radiation emitted by the semiconductor laser 12 and forming it into a collimating bean 28 of parallel rays. The collimated beam 28 is then passed through a sample chamber 30, and thereafter focussed by the lens 32 onto an active portion of a detector 34 that produces an output signal on the pins 36 and 38.

The prior art arrangement shown in FIG. 2 had several disadvantages. Usually, the extreme rays 22 and 24 diverged at such a wide angle that it was not feasible to collect all of the radiation emitted by the laser 12. Also, the highly collimated and coherent beam 28 was subject to undesirable interference effects caused by reflections from the windows 40 and 42 of the sample chamber 30. The interference effects could lead to erroneous results, particularly for gas samples that absorbed only weakly.

These undesirable features of the prior art arrangement have been completely overcome by the present invention. In addition, the sample chamber of the present invention permits elimination of the lens 26 and 32 as well as the windows 40 and 42, thereby greatly simplifying the sample chamber.

Figure 3:
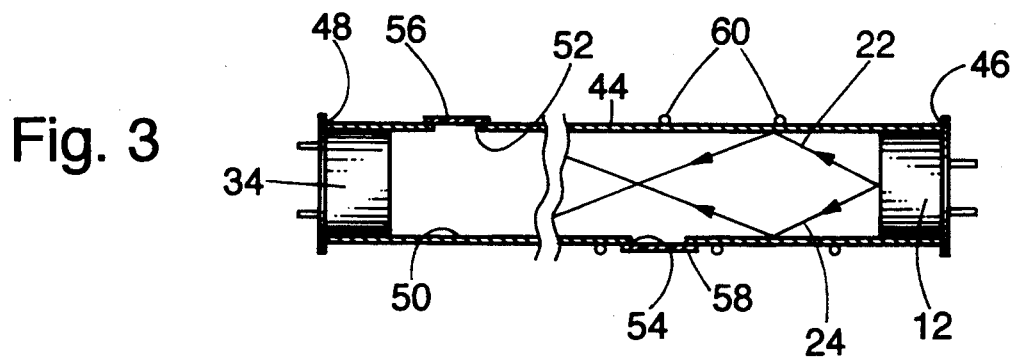
FIG. 3 is a diagrammatic cross sectional view of a gas sample chamber in accordance with a first preferred embodiment of the present invention.

FIG. 3 shows a sample chamber in accordance with a first preferred embodiment of the present invention.

In the first preferred embodiment of FIG. 3, the gas sample chamber includes an elongated hollow tube 44 having a first end 46 and a second end 48. The inside surface 50 of the hollow tube 44 is specularly reflective.

At least two apertures 52 and 54 are included in the hollow tube 44 to permit a gas that is to be sampled to diffuse into and out of the hollow tube 44. In this embodiment, the apertures 52 and 54 are covered by the semipermeable membranes 56 and 58. In the preferred embodiment, the semipermeable membrane consists of a thin sheet of silicone rubber. The semipermeable membrane serves as a very fine filter, keeping particles of a size greater than 0.1 micron from entering the tube 44 while not interfering with the free diffusion of gases into and out of the tube.

A semiconductor laser 12 is located at the first end 46 of the tube 44, and a detector 34 is located at the second end 48 of the tube 44. In an optional variation, an insulated heating wire 60 is wound around the tube 44 to warm the tube to prevent water vapor or other vapors from condensing on the inside surface 50.

In comparing the sample chamber of FIG. 3 with the prior art sample chamber of FIG. 2, it is apparent that a number of improvements result from the approach used in FIG. 3. The lenses 26 and 32 of FIG. 2 are eliminated along with the troublesome windows 40 and 42. Note that in FIG. 3 even the widely diverging emitted rays 22 and 24 are collected by the tube 44.

In the embodiment of FIG. 3, the active area of the detector 34 extends all the way across the tube 44, so that all of the radiation emitted by the laser 12 is collected by the detector 34, neglecting such loses as occur upon reflection from the inner surface 50.

Because collimated light is not used in the embodiment of FIG. 3, the undesirable interference effects referred to above are eliminated. It has been found that the active area of the detector 34 in the arrangement of FIG. 3 is illuminated in a surprisingly uniform manner, thereby rendering the output of the detector 34 independent of variations in sensitivity across its active area.

Figure 4:
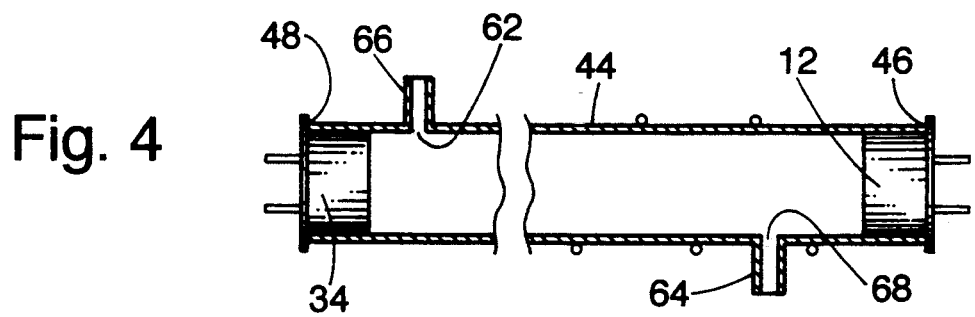
FIG. 4 is a diagrammatic cross sectional view of a gas sample chamber in accordance with a second preferred embodiment of the present invention.

FIG. 4 shows a second preferred embodiment of the sample chamber in accordance with the present invention. In the embodiment of FIG. 3, the gas to be measured diffused into and out of the sample chamber through the semipermeable membranes 56 and 58. In contrast, in the embodiment of FIG. 4, the gas to be measured is made to flow into the sample chamber through one of the ports 62 and 64 and out the other. Stub tubes 66 and 68 are provided to facilitate attachment of hoses or tubes that conduct the gas into and out of the sample chamber. In one variation, the gas flows from a pressurized source into the sample chamber through one of the ports 62 and 64 and is discharged into the atmosphere through the other port. In still another variation, the gas to be measured is drawn into the sample tube through one of the ports by means of a suction pump attached to the other port.

FIG. 5 shows a third preferred embodiment of the present invention. Like the embodiment of FIG. 3, the embodiment of FIG. 5 includes an elongated hollow tube 44 having a first end 46 and a second end 48. A semiconductor laser 12 is located at the first end 46, and a detector 34 is located at the second end 48. The entire inside surface 50 of the tube 44 is specularly reflective. In contrast to the embodiment of FIG. 3, a window 70 partitions the space within the tube 44 into a first section 72 and a second section 74.

In the embodiment of FIG. 5 (and the embodiment of FIG. 6) the semiconductor laser 12 is of a type, known in the prior art, that is tunable over a range of wavelengths. In this type of semiconductor laser, the wavelength of the radiation emitted can be varied by altering the temperature of the laser or by altering the drive current applied to the laser. Either or both techniques may be employed for purposes of the present invention. The laser 12 may be cooled by mounting it on a thermoelectric cooler. Both the temperature and the drive current can be servo controlled, and the techniques for doing this are well known in the art.

In the embodiments of FIGS. 5 and 6, the first section 72 is allocated to a first gas $G_1$, and the second section 74 is allocated to a second gas $G_2$.

Each of the gases $G_1$ and $G_2$ has at least one absorption band that uniquely identifies the gas. The window 70 is composed of a material that is practically transparent to radiation of wavelengths $\lambda_1$ and $\lambda_2$, where $\lambda_1$ is the wavelength corresponding to the absorption band of the gas $G_1$ and $\lambda_2$ is the wavelength of the absorption band of the gas $G_2$.

FIG. 7 is a graph showing the output of the detector 34 as the wavelength of the semiconductor laser 12 is varied through a range of wavelengths that includes $\lambda_1$ and $\lambda_2$. The concentration of the gas $G_1$ is related to the depth of the absorption band at the wavelength $\lambda_1$, and the concentration of the gas $G_2$ is related to the depth of the absorption band at the wavelength $\lambda_2$.

It is important to understand that the measurement technique described in connection with FIGS. 5, 6 and 7 is independent of how the gases $G_1$ and $G_2$ got into the first section 72 and the second section 74 respectively. This greatly broadens the applicability of the technique.

For example, one of the gases, exemplified by $G_1$ in FIG. 5 may be sealed within the first or second section, and could be pressurized. Such a sealed sample of gas may conveniently be used as a stable reference sample in one well-known measurement technique.

Another possibility is that either of the gases could be permitted to enter its chamber by free diffusion, as exemplified by the gas $G_2$ of FIG. 5. Typically, the semipermeable membranes 56 and 58 would be used to prevent undesirable particles from entering the second section 74 without interfering with the desired free diffusion.

A third possibility is exemplified by the gas $G_2$ in FIG. 6. Here the gas $G_2$ may be supplied through the stub tube 66 from a pressurized source, or may be drawn out through the stub tube 68 by a suction pump.

It can be seen that when the tube 44 is divided into two sections 72 and 74 by a window 70, there are nine different ways by which the gases $G_1$ and $G_2$ could have found their ways into the sections 72 and 74.

It is also noteworthy that the lengths of the first section 72 and second section 74 can be selected with regard to the relative abilities of the gases to absorb radiation, and with respect to the concentrations of the gases that are anticipated in a particular application of the technique.

In principle, the tube 44 could be partitioned into N sections by the use of N−1 windows.

Also, the wavelength range over which the semiconductor laser must be scanned can be greatly reduced by replacing the single semiconductor laser by N separate semiconductor lasers juxtaposed at the first end 46 of the tube 44, where N is the number of gases. FIG. 8 shows a source that includes two semiconductor lasers 76 and 78 in a single canister 80. FIG. 9 shows a source that includes two separate canisters 82 and 84 mounted on a common bulkhead 86 with each canister containing a single semiconductor laser.

Thus, there has been described a gas sample chamber that is particularly well suited for use with a semiconductor laser source of radiation. The sample chamber is noteworthy for its simplicity and for its ability to measure the concentration of more than one gas.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A gas sample chamber for use with a source of coherent radiation, comprising in combination:
   an elongated hollow tube having a first end and a second end and having an inside surface that is specularly reflective, and including means for permitting the gas sample to enter and leave the space within said elongated hollow tube;
   a semiconductor laser located at the first end of said elongated hollow tube and oriented to project radiation toward the second end;
   a detector located at the second end of said elongated hollow tube and occupying substantially the entire cross section of said elongated hollow tube.

2. The gas sample chamber of claim 1 wherein said means includes at least two spaced apertures.

3. The gas sample chamber of claim 2 wherein said at least two spaced apertures are each covered by a semipermeable membrane.

4. The gas sample chamber of claim 3 wherein said semipermeable membrane prevents particles larger than 0.1 micron from entering said elongated hollow tube while not interfering with diffusion of a gas into and out of said elongated hollow tube.

5. The gas sample chamber of claim 2 further comprising heating means for warming said elongated hollow tube to prevent condensation of gases or vapors on the inside surface of said elongated hollow tube.

6. A gas sample chamber for use with a source of coherent radiation, comprising in combination:
   an elongated hollow tube having a first end and a second end and having an inside surface that is specularly reflective;
   semiconductor laser means located at the first end of said elongated hollow tube, oriented to project radiation toward the second end, and producing radiation having a first wavelength $\lambda_1$ and a second wavelength $\lambda_2$;
   a window located between the first end and the second end of said elongated hollow tube, forming a gastight seal with the inside surface of said elongated hollow tube so as to partition said elongated hollow tube into a first section and a second section isolated from said first section, said window substantially transparent to radiation of wavelengths $\lambda_1$ and $\lambda_2$;
   first means for permitting a first gas to enter and leave the first section and second means for permitting a second gas to enter and leave the second section; and,
   a detector located at the second end of said elongated hollow tube and occupying substantially the entire cross section of said elongated hollow tube.

7. The gas sample chamber of claim 6 wherein said first means include at least two spaced ports.

8. The gas sample chamber of claim 6 wherein said second means include at least two spaced ports.

9. The gas sample chamber of claim 6 wherein said first means includes at least two spaced apertures.

10. The gas sample chamber of claim 9 wherein said at least two spaced apertures are each covered by a semipermeable membrane.

11. The gas sample chamber of claim 10 wherein said semipermeable membrane prevents particles larger than 0.1 micron from entering said elongated hollow tube while not interfering with diffusion of said first gas into and out of said elongated hollow tube.

12. The gas sample chamber of claim 6 wherein said second means include at least two spaced apertures.

13. The gas sample chamber of claim 12 wherein said at least two spaced apertures are each covered by a semipermeable membrane.

14. The gas sample chamber of claim 13 wherein said semipermeable membrane prevents particles larger than 0.1 micron from entering said elongated hollow tube while not interfering with diffusion of said second gas into and out of said elongated hollow tube.

15. The gas sample chamber of claim 6 further comprising heating means for warming said elongated hollow tube to prevent condensation of gases or vapors on the inside surface of said elongated hollow tube.

* * * * *